(12) United States Patent
Hruska et al.

(10) Patent No.: US 10,422,743 B2
(45) Date of Patent: Sep. 24, 2019

(54) SPECTROMETER WITH A RELAY LIGHTPIPE

(71) Applicant: VIAVI Solutions Inc., San Jose, CA (US)

(72) Inventors: Curtis R. Hruska, Cloverdale, CA (US); Benjamin F. Catching, Santa Rosa, CA (US); Marc K. Von Gunten, Santa Rosa, CA (US)

(73) Assignee: VIAVI Solutions Inc., San Jose, CA (US)

( * ) Notice: Subject to any disclaimer, the term of this patent is extended or adjusted under 35 U.S.C. 154(b) by 0 days.

(21) Appl. No.: 15/887,196

(22) Filed: Feb. 2, 2018

(65) Prior Publication Data

US 2018/0156723 A1    Jun. 7, 2018

Related U.S. Application Data

(63) Continuation of application No. 14/710,095, filed on May 12, 2015, now Pat. No. 9,885,655, which is a (Continued)

(51) Int. Cl.
*G01N 1/10* (2006.01)
*G01N 21/359* (2014.01)
(Continued)

(52) U.S. Cl.
CPC .......... *G01N 21/359* (2013.01); *G01J 3/0218* (2013.01); *G01J 3/0256* (2013.01);
(Continued)

(58) Field of Classification Search
CPC .. G01N 21/359; G01N 21/03; G01N 21/0303; G01N 21/70; G01N 21/8507;
(Continued)

(56) References Cited

U.S. PATENT DOCUMENTS 3,439,157 A   4/1969 Myles
4,054,389 A   10/1977 Owen et al.
(Continued)

FOREIGN PATENT DOCUMENTS

CA   2312529      1/2001
CN   101802573 A  8/2010
(Continued)

OTHER PUBLICATIONS

Extended European Search Report from corresponding European Application No. 13855627.9, dated Jun. 21, 2016, 7 pages.
(Continued)

*Primary Examiner* — Kara E. Geisel
*Assistant Examiner* — Jonathon Cook
(74) *Attorney, Agent, or Firm* — Harrity & Harrity, LLP

(57) ABSTRACT

A lightpipe is coupled to a spectrometer based on a laterally variable optical filter. The lightpipe may be used for both guiding the illuminating light towards a sample and collecting light reflected or emitted by the sample upon illumination, for spectral measurements at a distance from the sample afforded by the lightpipe. The lightpipe may include a slab of homogeneous transparent material for unconstrained bidirectional propagation of light in bulk of the material. The lightpipe may be solid, hollow, or sectioned for separated guiding of the illuminating and the reflected light.

20 Claims, 9 Drawing Sheets

Related U.S. Application Data continuation-in-part of application No. 14/079,280, filed on Nov. 13, 2013, now Pat. No. 9,234,839.

(60) Provisional application No. 61/992,082, filed on May 12, 2014, provisional application No. 61/784,811, filed on Mar. 14, 2013, provisional application No. 61/725,923, filed on Nov. 13, 2012.

(51) Int. Cl.
*G01J 3/02* (2006.01)
*G01J 3/10* (2006.01)

(52) U.S. Cl.
CPC .............. *G01J 3/0272* (2013.01); *G01J 3/10* (2013.01); *G01N 2201/0221* (2013.01); *G01N 2201/08* (2013.01)

(58) Field of Classification Search
CPC ........ G01N 2201/0221; G01N 2201/08; G01J 3/0218; G01J 3/0221; G01J 3/0256; G01J 3/0272; G01J 3/10
See application file for complete search history.

(56) References Cited

U.S. PATENT DOCUMENTS

| | | | |
|---|---|---|---|
| 4,127,773 A | 11/1978 | West et al. | |
| 4,195,932 A | 4/1980 | Popelka | |
| 4,382,656 A | 5/1983 | Gilby | |
| 4,835,389 A * | 5/1989 | Doyle | G01N 21/552 250/343 |
| 5,051,551 A * | 9/1991 | Doyle | G01N 21/552 250/341.2 |
| 5,065,025 A | 11/1991 | Doyle | |
| 5,166,755 A | 11/1992 | Gat | |
| 5,272,518 A | 12/1993 | Vincent | |
| 5,347,475 A | 9/1994 | Taylor et al. | |
| 5,418,366 A | 5/1995 | Rubin et al. | |
| 5,585,626 A | 12/1996 | Beck et al. | |
| 5,675,411 A | 10/1997 | Brooks et al. | |
| 5,736,410 A * | 4/1998 | Zarling | B82Y 15/00 250/458.1 |
| 5,851,181 A | 12/1998 | Talmor | |
| 5,946,088 A * | 8/1999 | Aldridge | B01F 9/0005 356/300 |
| 6,271,521 B1 * | 8/2001 | Saathoff | G01N 21/359 250/339.07 |
| 6,324,418 B1 | 11/2001 | Crowley et al. | |
| 6,373,574 B1 | 4/2002 | Gu et al. | |
| 6,420,708 B2 | 7/2002 | Wilks, Jr. et al. | |
| 6,473,165 B1 | 10/2002 | Coombs et al. | |
| 6,791,688 B2 * | 9/2004 | Lai | B01F 15/00207 250/458.1 |
| 6,903,813 B2 | 6/2005 | Jung et al. | |
| 7,006,204 B2 | 2/2006 | Coombs et al. | |
| 7,033,056 B2 | 4/2006 | Andersen et al. | |
| 7,057,722 B2 * | 6/2006 | Gehrlein | G01N 21/3563 356/328 |
| 7,075,645 B2 * | 7/2006 | Gehrlein | B01F 3/02 356/328 |
| 7,113,265 B1 | 9/2006 | Sarrazin | |
| 7,184,133 B2 | 2/2007 | Coombs et al. | |
| 7,218,395 B2 * | 5/2007 | Kaye | B07C 5/344 356/301 |
| 7,252,399 B2 | 8/2007 | Ferri et al. | |
| 7,420,663 B2 | 9/2008 | Wang et al. | |
| 7,671,985 B1 | 3/2010 | Milesevic et al. | |
| 7,839,504 B1 | 11/2010 | Newbury | |
| 7,907,282 B2 | 3/2011 | Coates | |
| 8,159,668 B2 | 4/2012 | Malinen et al. | |
| 8,242,462 B2 | 8/2012 | Jaffe et al. | |
| 8,358,418 B2 | 1/2013 | Myrick et al. | |
| 8,360,771 B2 | 1/2013 | Stookey | |
| 8,373,857 B2 | 2/2013 | Jung et al. | |
| 8,455,827 B1 | 6/2013 | Chiao et al. | |
| 9,234,839 B2 | 1/2016 | Hruska et al. | |
| 9,671,330 B2 | 6/2017 | Hruska et al. | |
| 9,885,655 B2 | 2/2018 | Hruska et al. | |
| 2002/0020748 A1 | 2/2002 | Gu et al. | |
| 2002/0131047 A1 | 9/2002 | Zarrabian et al. | |
| 2002/0190213 A1 | 12/2002 | Bynum | |
| 2003/0071998 A1 | 4/2003 | Krupka et al. | |
| 2003/0122081 A1 | 7/2003 | Herrera et al. | |
| 2003/0156283 A1 | 8/2003 | Jung et al. | |
| 2005/0007596 A1 | 1/2005 | Wilks, Jr. et al. | |
| 2006/0044833 A1 | 3/2006 | Li | |
| 2006/0240573 A1 * | 10/2006 | Kao | G01N 21/78 436/524 |
| 2009/0195776 A1 | 8/2009 | Durst et al. | |
| 2010/0092083 A1 | 4/2010 | Herloski et al. | |
| 2010/0290042 A1 | 11/2010 | Vakhshoori et al. | |
| 2011/0281367 A1 | 11/2011 | Walte et al. | |
| 2012/0056093 A1 | 3/2012 | Poteet et al. | |
| 2012/0184827 A1 | 7/2012 | Shwartz | |
| 2012/0188541 A1 | 7/2012 | Demmer et al. | |
| 2013/0079254 A1 | 3/2013 | Azimi et al. | |
| 2014/0045250 A1 | 2/2014 | Kreifels et al. | |
| 2014/0049615 A1 | 2/2014 | Uwagawa | |
| 2014/0085623 A1 | 3/2014 | Lorbeer et al. | |
| 2014/0247442 A1 | 9/2014 | Johnson | |
| 2015/0204833 A1 | 7/2015 | O'Brien et al. | |
| 2017/0336319 A1 | 11/2017 | Hruska et al. | |

FOREIGN PATENT DOCUMENTS

| | | |
|---|---|---|
| EP | 0422448 | 11/1995 |
| JP | S53-146112 U | 4/1952 |
| JP | S57-108721 A | 7/1982 |
| JP | S57-190431 U | 12/1982 |
| JP | H02302633 A | 12/1990 |
| JP | H09-15048 A | 1/1997 |
| JP | H1085222 A | 4/1998 |
| JP | 2004-125824 A | 4/2004 |
| JP | 2005-274270 A | 10/2005 |
| JP | 2011-253078 A | 12/2011 |
| JP | 2012-141442 A | 7/2012 |
| TW | M400587 U | 3/2011 |
| TW | 201321726 A | 6/2013 |
| WO | WO 2009/012352 | 1/2009 |
| WO | WO 2009/030812 A1 | 3/2009 |
| WO | WO 2012/080478 | 6/2012 |
| WO | WO 2012/090675 A1 | 7/2012 |

OTHER PUBLICATIONS

International Search Report from corresponding PCT application No. PCT/US2013/069910, dated Apr. 4, 2014, 6 pages.

* cited by examiner

SPECTROMETER WITH A RELAY LIGHTPIPE

CROSS-REFERENCE TO RELATED APPLICATIONS

This application is a continuation of U.S. patent application Ser. No. 14/710,095, filed May 12, 2015 (now U.S. Pat. No. 9,885,655), which is a continuation-in-part from U.S. patent application Ser. No. 14/079,280, filed Nov. 13, 2013 (now U.S. Pat. No. 9,234,839), which claims priority from U.S. Provisional Patent Application No. 61/725,923, filed Nov. 13, 2012, and 61/784,811, filed Mar. 14, 2013. U.S. patent application Ser. No. 14/710,095 claims priority from U.S. Provisional Patent Application No. 61/992,082, filed May 12, 2014; the disclosures of which are incorporated herein by reference.

TECHNICAL FIELD

The present disclosure relates to optical test and measurement, and in particular to portable optical spectrometers.

BACKGROUND

A laterally variable optical filter (LVF) may include a transmission optical filter having a transmission wavelength varying in a transverse direction across a surface of the filter. A compact optical spectrometer may be constructed by coupling a photodetector array to an LVF. When the LVF surface is illuminated with light reflected by the sample, light portions at individual wavelengths are selectively transmitted through the LVF and detected by individual pixels of the photodetector array. As a result, a reflection spectrum of the sample may be obtained. A miniature light source may be provided in an LVF-based spectrometer for illuminating a sample, enabling quick, on-the-spot reflection spectral measurements.

Due to their miniature size and small weight, LVF-based spectrometers may be constructed in handheld configuration, making them suitable for use in a variety of test and measurement applications. It is sufficient to bring such a handheld LVF-based spectrometer in close proximity with the sample, and to press a thumb-operated button on the back of the spectrometer to quickly (within seconds, or even less than a second) obtain a reflection spectrum. Other types of spectra, e.g. fluorescence, transmission, etc., may also be obtained with a suitable configuration of the light source.

A direct contact between the handheld spectrometer and the sample may be undesirable. For instance, chemically aggressive samples, extremely hot or cold samples, biohazardous samples, etc., may damage the compact spectrometer or endanger the user. In other applications, such as food processing, a direct physical contact may be undesirable for hygienic reasons. For applications such as these, a remote spectra collection may be preferable.

To obtain a spectrum from a safe distance, the illuminating light may be formed into a parallel or converging beam of light by a lens-based or mirror-based collimator, so as to concentrate the illuminating light on the sample. A mirror or lens, or a lens system, may be used to remotely collect light reflected by the sample. Alternatively, a pair of optical fibers may be used to bring the illuminating light to the sample, and to guide the reflected light back into a spectrometer for a spectral measurement.

Free-space or fiber-guided illumination delivery and light collection systems have some drawbacks. For repeatability purposes, a free-space collection system needs to be placed at a pre-defined distance from the sample, which may not be convenient, or may even be unfeasible when holding the spectrometer by hand. Light collection systems based on optical fibers typically require precision optical alignment for coupling light into the illuminating fiber, and may require dedicated optics, so-called "optical head", for coupling the reflected light into a core of the light collection fiber. Transmission of a fiber bundle may depend on its bend radius, requiring re-calibration if the fiber bundle is re-shaped or bent at a different radius. Furthermore, most optical fibers are fragile and expensive, and may require replacement upon damage of sensitive fiber tips caused by chemically aggressive, hot, cold, or abrasive samples.

SUMMARY

In accordance with an aspect of the disclosure, a length of a lightpipe, herein termed a "relay lightpipe", may be used for conducting illuminating light to the sample, and for collecting (relaying) light reflected or emitted by the sample back to an LVF-based spectrometer. A relay lightpipe may include a slab of a transparent material for unconstrained propagation of light in bulk of the material, or it may be hollow. A relay lightpipe may also be straight or pre-curved. Due to relative insensitivity of an LVF-based spectrometer to a solid angle and spot size of the emitted or reflected light, meaningful spectral data may be obtained even when a same slab of transparent material is used for guiding both the illuminating and reflected light in opposite directions, so that the optical paths of the illuminating and reflected light overlap in the slab. In other words, the illuminating light may be guided by the relay lightpipe towards the sample, and the reflected light may be guided by the relay lightpipe towards the spectrometer, so that optical paths of the illuminating light and the reflected light may overlap in the relay lightpipe. The length of the relay lightpipe may be selected to be sufficiently long to enable a direct illumination and collection of light reflected or emitted by a hot or cold sample, while keeping temperature-sensitive spectrometer electronics away from the hot or cold sample.

In accordance with an aspect of the disclosure, there is provided an apparatus for obtaining an optical spectrum of a sample, the apparatus comprising:

a spectrometer comprising: a housing comprising an outer surface; a light source within the housing for illuminating the sample with illuminating light; and a spectral engine within the housing for obtaining the optical spectrum of the sample illuminated with the illuminating light, wherein the spectral engine comprises a laterally variable optical filter coupled to a photodetector array, wherein the light source and the spectral engine are optically coupled to an opening or transparent window in the outer surface; and a relay lightpipe extending between proximal and distal ends thereof and configured for unconstrained propagation of the illuminating light in bulk of the relay lightpipe from the proximal to the distal end when the proximal end is optically coupled to the light source and the spectral engine via the opening or transparent window, and wherein the distal end is configured for contacting or inserting into the sample;

wherein the relay lightpipe is configured for collecting signal light emanating from the sample when the sample is illuminated with the illuminating light via the relay lightpipe, and for unconstrained propagation of the signal light in bulk of the relay lightpipe back from the distal end to the proximal end, for delivery to the spectral engine, thereby enabling the spectrometer to obtain the optical spectrum of the sample at a distance from the sample.

In one embodiment, the relay lightpipe may include a slab of homogeneous transparent material extending between the proximal and distal ends, such that optical paths of the illuminating and signal light at least partially overlap in the slab. In another embodiment, the relay lightpipe may be sectioned, i.e. the relay lightpipe may include first and second slabs of homogeneous transparent material extending between the proximal and distal ends and running adjacent and parallel to each other. The first slab may be configured for propagating the illuminating light therein from the proximal end to the distal end, and the second slab may be configured for propagating the signal light therein from the distal end to the proximal end. The distal end of the relay lightpipe may be chiseled or lensed, for focusing the illuminating light on the sample, and for collecting the signal light from the sample.

For samples including a granular material such as seeds, powders, etc., material capable of mixing or flowing, or for samples comprising fluids, including fluid suspensions, emulsions, etc., the apparatus may include a container for holding the granular or fluid material, and a vibration transducer for vibrating the granular or fluid material. For example, the vibration transducer ma be operably coupled to the container for vibrating the container. The container may include an opening for inserting the relay lightpipe into the granular or fluid material for obtaining an optical spectrum of the granular or fluid material, while the vibration transducer vibrates the container, thereby causing moving and mixing of the granular or fluid material. The moving and mixing of the granular or fluid material may help average reflection spectra being obtained, thereby making the reflection spectra less dependent on a random configuration of the granular or fluid material at the spot of illumination.

In accordance with the disclosure, there is further provided an apparatus for obtaining an optical transmission spectrum of a sample comprising a granular or fluid material, the apparatus comprising:

a spectrometer comprising a housing comprising an outer surface and a spectral engine within the housing for obtaining a light spectrum of the sample illuminated with the illuminating light, wherein the spectral engine comprises a laterally variable optical filter coupled to a photodetector array, wherein the spectral engine is optically coupled to an opening or transparent window in the outer surface;

a relay lightpipe extending between proximal and distal ends thereof and configured for unconstrained propagation of light in bulk of the relay lightpipe between the proximal and distal ends, wherein the relay lightpipe is connectable to the housing so that the proximal end is disposed against the opening or transparent window, for optical coupling the relay lightpipe to the spectral engine, and wherein the distal end is configured for contacting or inserting into the granular or fluid material;

a container for holding the sample, wherein the container comprises a window at a bottom thereof;

a vibration transducer operably coupled to the container for vibrating the granular or fluid material; and a light source optically coupled to the window, for illuminating the sample with illuminating light through the window while the vibration transducer vibrates the container thereby causing moving and mixing of the granular or fluid material;

wherein the relay lightpipe is configured for collecting signal light emanating from the mixing and moving granular or fluid material illuminated with the illuminating light, and for conducting the signal light back from the distal end to the proximal end, for delivery to the spectral engine, thereby enabling the spectrometer to obtain the transmission spectrum of the sample at a distance from the sample.

In one embodiment, the relay lightpipe comprises a first opening therein extending therethrough in a direction transversal to the illuminating light, the apparatus further comprising a calibration element insertable into the first opening, wherein the calibration element comprises a reflectance reference section for registering with the first opening when the calibration element is inserted into the first opening, so as to reflect the illuminating light back to the proximal end of the relay lightpipe for detection by the spectrometer.

In accordance with the disclosure, there is further provided a method for obtaining an optical spectrum of a sample, the method comprising:

bringing near the sample, contacting the sample, or inserting into the sample a relay lightpipe of a spectrometer, wherein the spectrometer comprises a housing comprising an outer surface, a light source within the housing for illuminating the sample with illuminating light, and a spectral engine within the housing for obtaining the optical spectrum of the sample illuminated with the illuminating light, wherein the spectral engine comprises a laterally variable optical filter coupled to a photodetector array, wherein the light source and the spectral engine are optically coupled to an opening or transparent window in the outer surface;

wherein the relay lightpipe extends between proximal and distal ends thereof and is configured for unconstrained propagation of light in bulk of the relay lightpipe between the proximal and distal ends, wherein the relay lightpipe is optically coupled to the light source and the spectral engine via the opening or transparent window;

conducting the illuminating light in the relay lightpipe from the proximal end to the distal end thereof for illuminating the sample, collecting signal light emanating from the sample illuminated with the illuminating light wherein the signal light is collected via the distal end of the relay lightpipe, conducting the signal light back from the distal end to the proximal end and further to the spectral engine via the relay lightpipe; and obtaining the optical spectrum of the sample at a distance from the sample.

BRIEF DESCRIPTION OF THE DRAWINGS

Exemplary embodiments will now be described in conjunction with the drawings, in which.

DETAILED DESCRIPTION

While the present teachings are described in conjunction with various embodiments and examples, it is not intended that the present teachings be limited to such embodiments. On the contrary, the present teachings encompass various alternatives and equivalents, as will be appreciated by those of skill in the art.

Figure 1A:
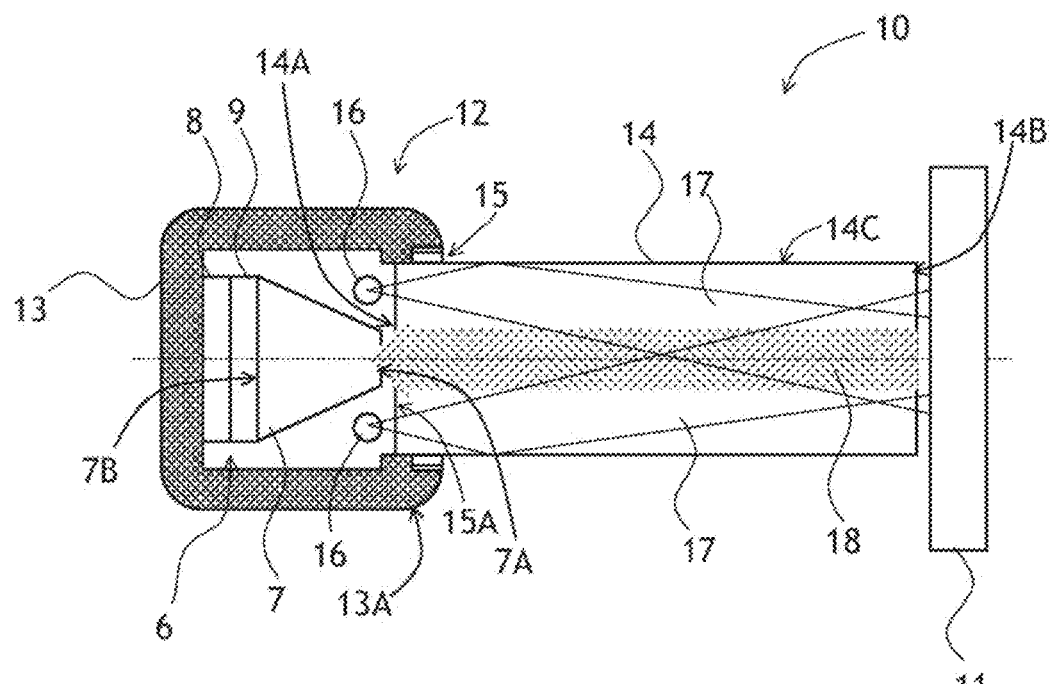
FIG. 1A illustrates a schematic side cross-sectional view of an apparatus of the present disclosure for obtaining an optical spectrum of a sample, the apparatus including a homogeneous relay lightpipe having flat ends.
Figure 1B:
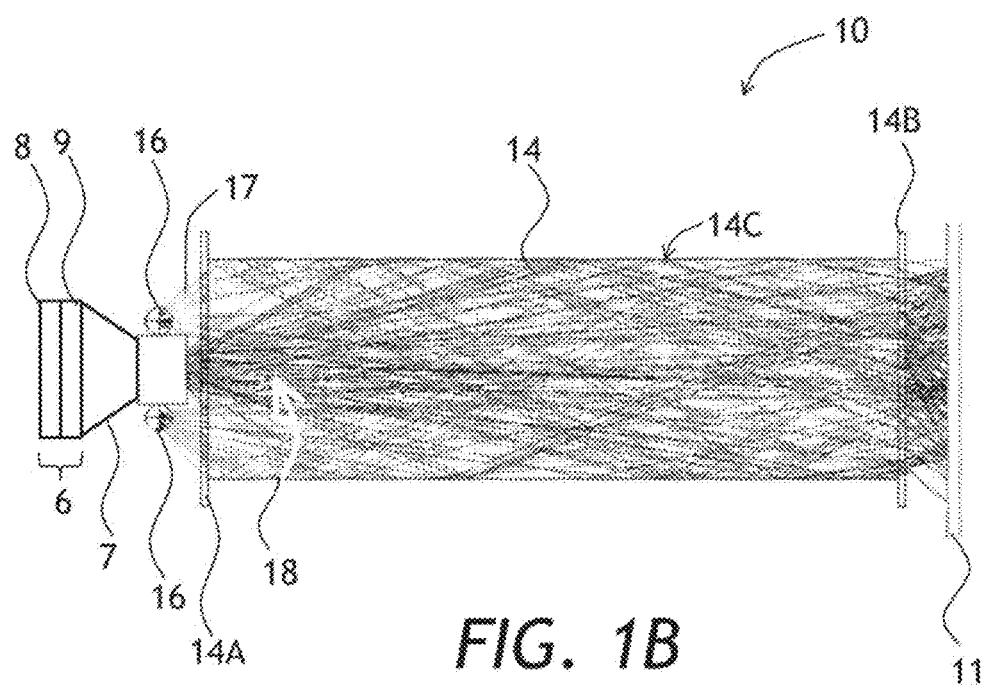
FIG. 1B illustrates a ray-tracing simulation of the apparatus of FIG. 1A.
Figure 1C:
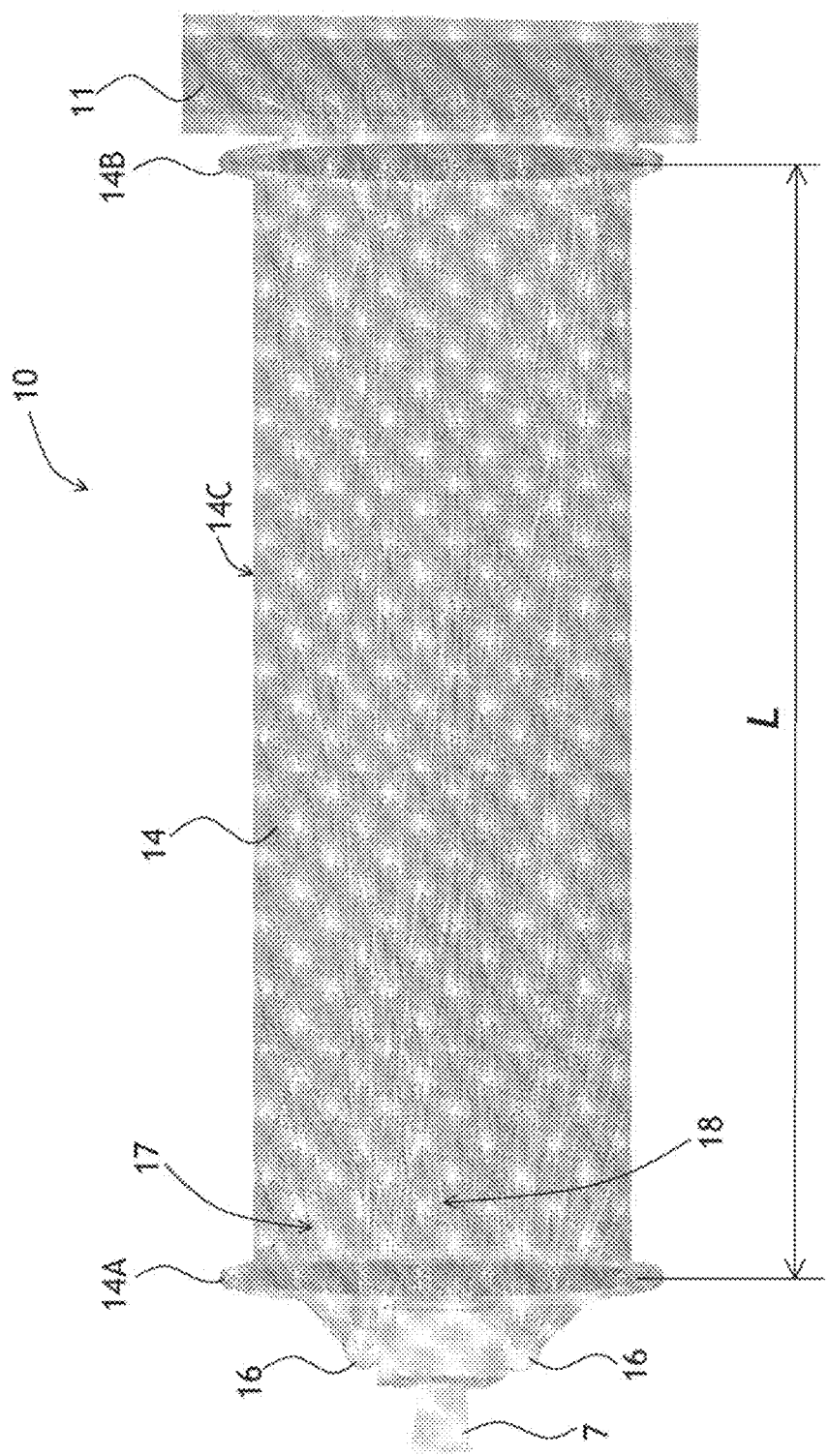
FIG. 1C illustrates a three-dimensional view of the ray-tracing simulation of FIG. 1B.

Referring to FIGS. 1A, 1B, and 1C, an apparatus 10 for obtaining an optical spectrum of a sample 11 may include a spectrometer 12 having a housing 13 (FIG. 1A). The apparatus 10 may further include a relay lightpipe 14, which may be attached to the housing 13 by means of an optional coupler 15. The optical coupler 15 may include, for example, a threaded opening 15A in the housing 13. The spectrometer 12 may include a pair of light bulbs 16 disposed within the housing 13, for illuminating the sample 11 with illuminating light 17. Another light source or sources, e.g. light emitting diodes (LED), may be used instead of the pair of light bulbs 16. One light bulb 16 may be used. The spectrometer 12 may further include a spectral engine 6 disposed within the housing 13, for obtaining the optical spectrum of the sample 11. The spectral engine 6 may include a laterally variable optical filter (LVF) 9 coupled to a photodetector array 8. The light bulbs 16 and the spectral engine 6 may be optically coupled to the opening 15A or an optional transparent window, not shown, in an outer surface 13A of the housing 13. Due to the compactness of the spectral engine and the photodetector array 8, the spectrometer 12 may be portable or handheld, and may have dimensions of less than 15 cm×15 cm×15 cm, and having a weight of less than 2 kg.

The relay lightpipe 14 extends between its proximal 14A and distal 14B ends. The proximal end 14A of the relay lightpipe 14 may be optically coupled to the opening 15A in the outer surface 13A. The distal surface 14B may be optically coupled to the sample 11. The relay lightpipe 14 may be configured to provide unconstrained propagation of light in bulk of the relay lightpipe 14 between the proximal 14A and distal 14B ends. In other words, light may propagate in the relay lightpipe as a free, non-guided wave, being limited only by reflections from walls i.e. without any guiding elements having a non-uniform refractive index for guiding light, such as optical fibers.

The function of the threaded coupler 15 is to affix the relay lightpipe 14 to the housing 13 so that the proximal end 14A of the relay lightpipe 14 is disposed within or adjacent the opening 15A or the optional window, for optical coupling the relay lightpipe 14 to the light bulbs 16 and the spectral engine 6. Other types of couplers, e.g. a cam-based coupler, a friction-based coupler, a lockable ledge-based coupler, etc. may be used instead of the threaded coupler 15. The purpose of the threaded coupler 15, or a similar coupler, may be to quickly replace the relay lightpipe 14 with another relay lightpipe 14 of a different length or shape, or the same length L e.g. when the previous relay lightpipe 14 becomes contaminated or damaged in the process of measuring the optical spectrum of the sample 11.

When affixed, the relay lightpipe 14 is optically coupled to the light bulbs 16 and the spectral engine 6. The relay lightpipe 14 may be configured for conducting the illuminating light 17 from the proximal 14A end to the distal end 14B. The proximal end 14A of the relay lightpipe 14 may include a substantially flat surface for optically coupling to the opening 15A, or a transparent window if any, in the outer surface 13A of the housing 13. The distal end 14B of the relay lightpipe 14 may be configured for bringing near, contacting, and/or inserting into the sample 11, so that signal light 18 emanating from the sample 11 upon illumination with the illuminating light 17, may be collected by the distal end 14B of the relay lightpipe 14. The collected signal light 18 may propagate back from the distal end 14B to the proximal end 14A of the relay lightpipe 14, for delivery to the spectral engine 6 via an optional tapered light pipe (TLP) 7. The TLP 7 may extend between narrow 7A and wide 7B ends of the TLP 7. The wide end 7A may be optically coupled to the LVF 9, and the narrow end 7B may be disposed proximate the opening 15A, or window if provided, in the outer surface 15 of the housing 13. A more detailed description of the spectrometer 12 is provided in U.S. patent application Ser. No. 14/079,280, which is incorporated herein by reference.

The spectrometer 12 may obtain an optical spectrum of the sample 11, e.g. a reflection or fluorescence spectrum. The relay lightpipe 14 enables the optical spectrum to be measured from a distance from the sample 11 approximately equal to a length L of the relay lightpipe 14 (FIG. 1C). In one embodiment, the length L is at least 8 mm to ensure an adequate distance to a food sample, for example. The length L may be over 50 mm, and even over 200 mm in some embodiments e.g. where a chemically active, hot, or cold samples need to be measured. The length L may be limited by an absorption loss in the bulk of the relay lightpipe 14, and/or by a surface scattering or transmission loss of reflecting surface(s) of the relay light pipe 14.

The relay lightpipe 14 shown in FIG. 1C has a circular cross-section having a cylindrical outer wall 14C extending between the proximal 14A and distal 14B flat surfaces. The relay lightpipe 14 is not limited to a circular cross-section, for example the relay lightpipe 14 may have oval, rectangular, or polygonal cross-section. The relay lightpipe 14 may have a diameter or a lateral size of at least 2 mm, more preferably at least 5 mm. The relay lightpipe 14 shown in FIGS. 1A to 1C may be a slab of a homogeneous transparent material extending between the proximal 14A and distal 14B substantially flat optical surfaces. Glass, acrylic, or another transparent material may be used. In one embodiment, the relay lightpipe 14 has a large enough refractive index, e.g. 1.6 or more, so that a substantial portion, e.g., at least 80%, of optical power of the illuminating 17 and the signal 18 light entering the relay lightpipe 14 and propagating between the proximal 14A and distal 14B flat surfaces, is retained in the relay lightpipe 14 by total internal reflection (TIR) from the outer wall 14C. Rays at angles of incidence smaller than a TIR, critical angle may escape the relay lightpipe 14. To improve overall reflectance, the outer wall 14C may be mirrored to provide near 100% reflectivity even for the rays at small angles of incidence.

The relay lightpipe 14 may have more than one wall. For example, the relay lightpipe 14 may have triangular, rectangular, or polygonal shaped cross section, such that the relay lightpipe 14 may have three, four, and more outer walls. Furthermore, the relay lightpipe 14 may be hollow and optionally include a reflective inner wall. The relay lightpipe 14 may also include a permanently bent section, not shown, between, proximal 14A and distal 14B ends of the relay lightpipe 14.

Figure 1D:
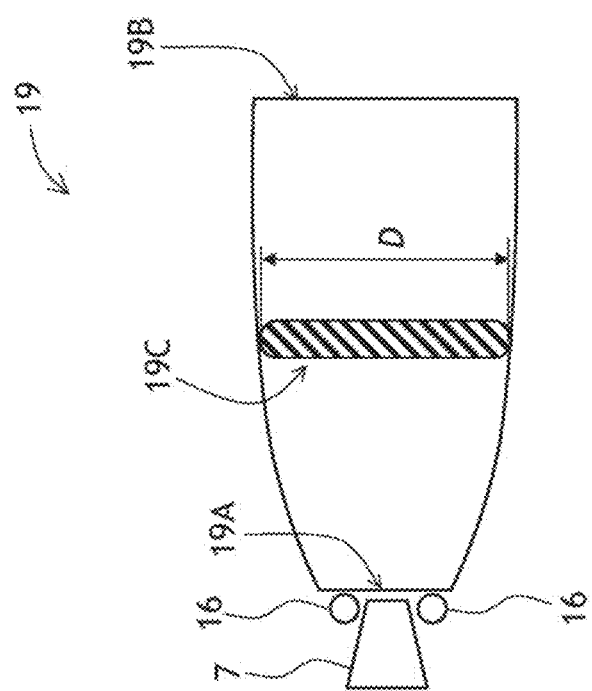
FIG. 1D illustrates a plan view of an embodiment of a relay lightpipe for use in the apparatus of FIG. 1A.

In the embodiments shown in FIGS. 1A to 1C, the relay lightpipe 14 has a cross-section that is substantially constant between the proximal 14A and distal 14B ends of the relay lightpipe 14. The relay lightpipe 14 may also be tapered. Referring to FIG. 1D with further reference to FIGS. 1A to 1C, a tapered relay lightpipe 19 is shown with the light bulbs 16 and the TLP 78. The tapered relay lightpipe 19 (FIG. 1D) widens in going from its proximal 19a to the distal 19B end; that is, a width D of a cross-section 19C of the tapered relay lightpipe 19 may increase in going from the proximal 19a to the distal 19B ends. The tapered shape may facilitate obtaining a more averaged spectrum of the sample 11, because a larger area of the sample 11 may be illuminated due to the wider distal end 19B, and the signal light 18 may be accordingly collected from the larger area of the sample 11. The tapered relay lightpipe 19 may function as a non-imaging concentrator of light, for example a compound parabolic concentrator of light. To that end, a sidewall 19D of the tapered relay lightpipe 19 may be curved as shown in FIG. 1D, so that the width D of the cross-section 19C increases in a non-linear fashion in going from the proximal 19a to the distal 19B end of the tapered relay lightpipe 19.

Optical paths of the illuminating 17 and signal 18 light may overlap in the slab 14, as shown in the simulations of FIGS. 1B and 1C. Even thought the optical paths of the illuminating 17 and signal 18 light may partially overlap, the spectral engine 6 is able to obtain a reflection spectrum with a good, e.g. better than 20 dB, signal-to-noise ratio. This unexpected and advantageous feature may be related to a relative insensitivity of an LVF-based spectrometer, such as the spectrometer 12, to a solid angle of the signal light 18, e.g. emitted or reflected light, at the LVF 9. The TLP 7 has a property of reducing the solid angle as the signal light 18 propagates from the narrow end 7A to the wide end 7B of the TLP 7, which further relaxes the requirement of the solid angle of the signal light 18.

Figure 2:
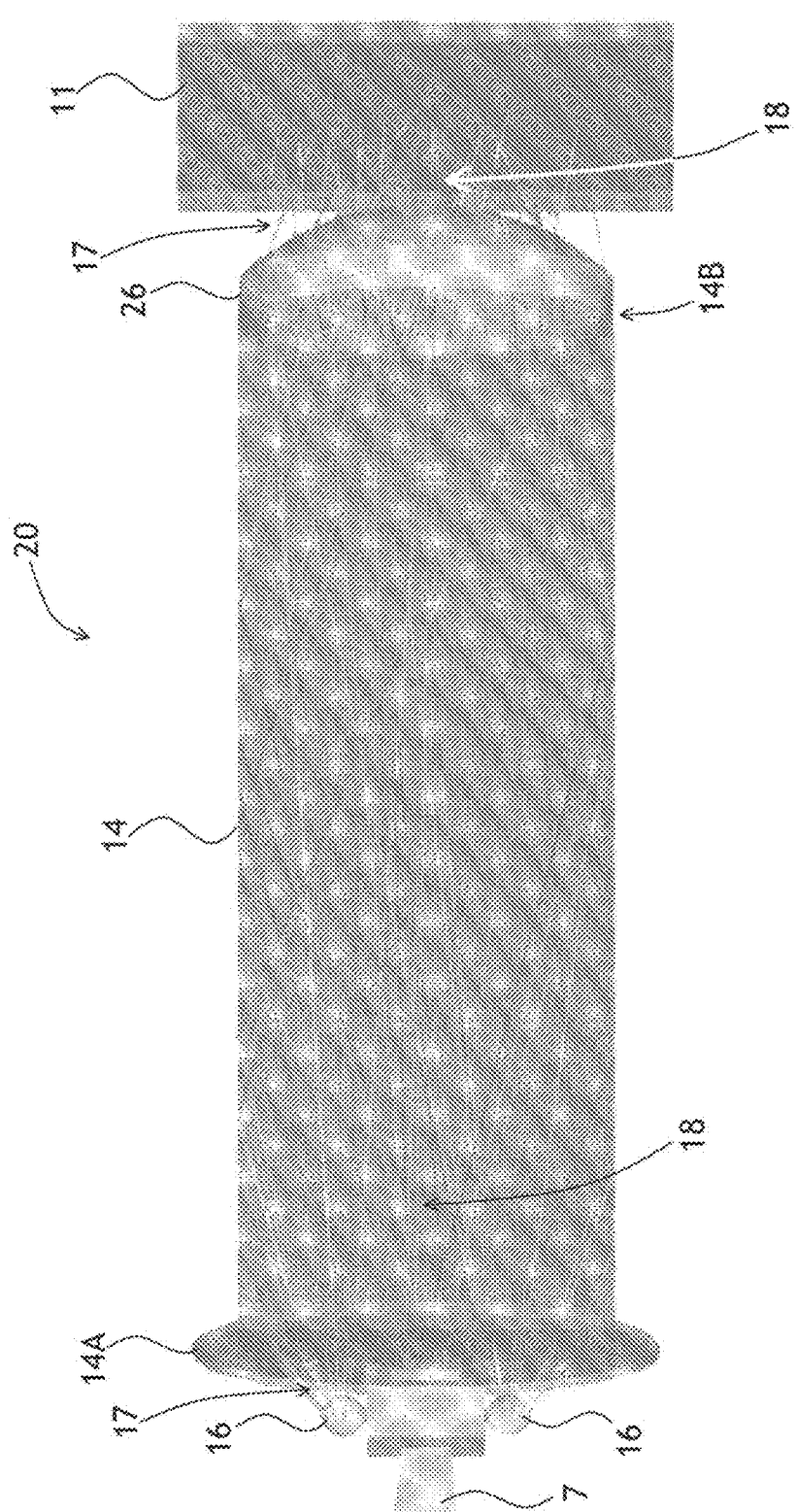
FIG. 2 illustrates a three-dimensional view of a ray-tracing simulation of an apparatus for obtaining an optical spectrum of a sample, the apparatus including a relay lightpipe having a lens at the distal end.

Referring now to FIG. 2 with further reference to FIGS. 1A-1C, an apparatus 20 for obtaining an optical spectrum of the sample 11 is similar to the apparatus 10 of FIGS. 1A-1C. One difference of the apparatus 20 of FIG. 2 is that the slab 14 may end with a lens element 26 optically coupled to the distal end 14B far focusing the illuminating light 17 on the sample 11, and/or for collecting the signal light 18 from the sample 11. In one embodiment, instead of the lens element 26, the distal end 14B itself may be chiseled or lensed.

Figure 3A:
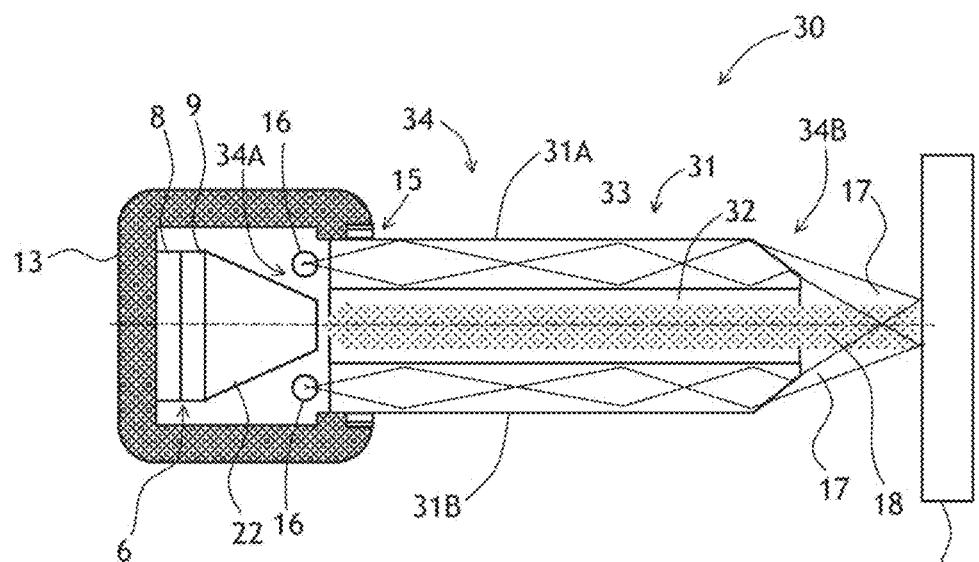
FIG. 3A illustrates a schematic side cross-sectional view of an apparatus for obtaining an optical spectrum of a sample, the apparatus including a sectioned chiseled relay lightpipe.
Figure 3B:
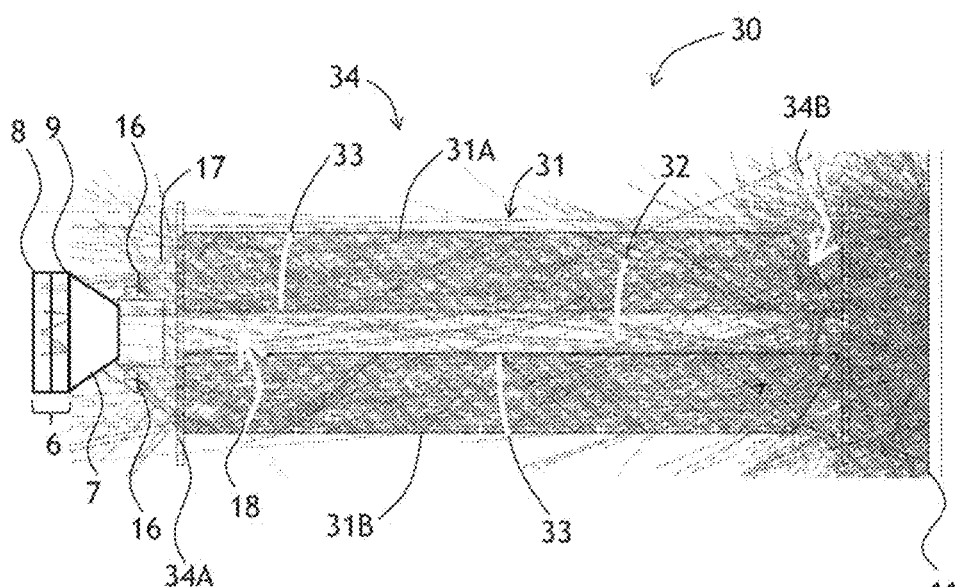
FIG. 3B illustrates a ray-tracing simulation of the apparatus of FIG. 3A.

Turning now to FIGS. 3A and 3B with further reference to FIGS. 1A-1C and FIG. 2, an apparatus 30 for obtaining an optical spectrum of the sample 11 is similar to the apparatus 10 of FIGS. 1A-1C and the apparatus 20 of FIG. 2. One difference of the apparatus 30 of FIGS. 3A and 3B is that a sectioned relay lightpipe 34 is provided instead of the homogeneous lightpipe 14 of FIGS. 1A-1C and FIG. 2. The sectioned relay lightpipe 34 of FIGS. 3A and 3B includes first 31 and second 32 slabs of a homogeneous transparent material extending between proximal 34A and distal 34B ends of the sectioned relay lightpipe 34 and running adjacent and parallel to each other. The first slab 31 may optionally include first 31A and second 31B portions, the second slab 32 being disposed in between the first 31A and second 31B portions of the first slab 31. The first slab 31 may be configured for propagating the illuminating light 17 from the proximal end 34A to the distal end 34B, and the second slab 32 may be configured for propagating the signal light 18 from the distal end 34B to the proximal end 34A. The first slab 31 including the first 31A and second 31B portions, and the second slab 32 may have e.g. rectangular cross sections, or alternatively the first slab 31 may have an annular cross section, and the second slab 32 may have an circular cross section surrounded by the annular cross section of the first slab 31.

The first 31 and/or second 32 slabs may include at least one mirrored side 33 extending between the proximal 34A and distal 34B ends, for a better separation of the illuminating light 17 and the signal light 18. Outer sides of the first slab 31 may also be mirrored for a better retaining of the illuminating light 17 in the first slab 31. The first slab 31 may be chiseled at the distal end 34B of the relay lightpipe 34, for concentrating the illuminating light 17 on the sample 11.

Figure 4A:
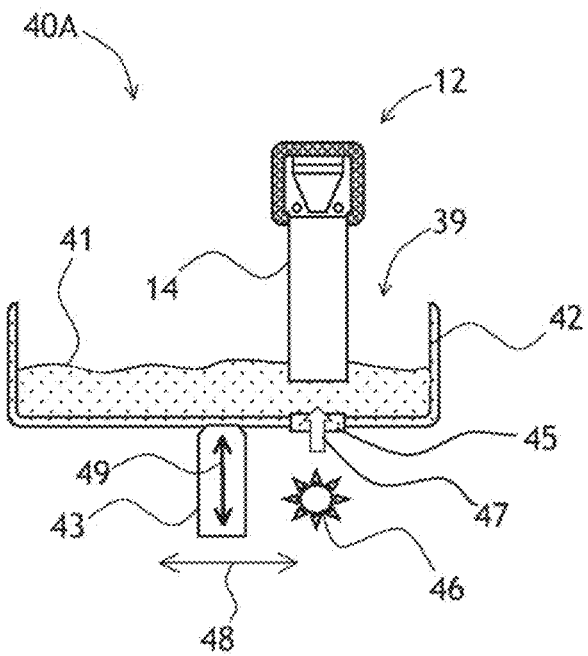
FIG. 4A illustrates a schematic side cross-sectional view of an apparatus for obtaining a reflection optical spectrum of a granular sample.

Referring to FIG. 4A, an apparatus 40A for obtaining a reflection spectrum of a granular material, such as seeds, grains, sands, powders, etc., capable of flowing and mixing, is presented. Various fluid materials such as suspensions, emulsions, etc., may also be measured by the apparatus 40A. The apparatus 40A includes the spectrometer 12 equipped with the relay lightpipe 14 of FIGS. 1A-1C or FIG. 2. The relay lightpipe 34 of FIGS. 3A and 3B may also be used. The apparatus 40A may further include a container 42 for holding granular or fluid material 41, and a vibration transducer 43 operably coupled to the container 42 for vibrating the container 42. The container 42 may include an open end 39, or merely an opening for inserting the relay lightpipe 14 into the granular or fluid material 41 for obtaining an optical spectrum of the granular or fluid material 41. As the optical spectrum is being collected, the vibration transducer 43 may vibrate the container 42, thereby causing moving and/or mixing of the granular or fluid material 41. The moving and/or mixing the granular or fluid material 41 under the distal end 14B of the relay lightpipe 14 may result in averaging of the reflection spectra being collected, which may lessen the influence of shape and position of individual particles (grains fluid-suspended particles, etc.) of the granular or fluid material 41 under the relay lightpipe 14, making the reflection spectra collected by the spectrometer 12 more reproducible. The larger the cross-section of the relay lightpipe 34, the larger averaging effect may be. In one embodiment, the vibration transducer 43 may vibrate the granular or fluid material 41 directly.

For transreflection measurements, the container 42 may include an optional window 45 at the bottom, and an additional light source 46 may be optically coupled to the window 45, for illuminating the granular or fluid material 41 through the window 45 while the vibration transducer 43 vibrates the granular or fluid material 41, thereby causing moving and mixing of the granular or fluid material 41.

Figure 4B:
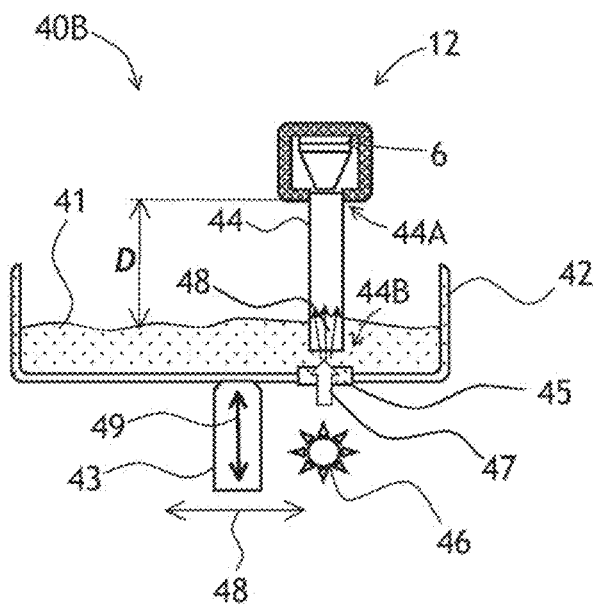
FIG. 4B illustrates a schematic side cross-sectional view of an apparatus for obtaining a transmission optical spectrum of a granular sample.

Transmission spectra of the granular or fluid material 41 may also be obtained. Referring now to FIG. 4B, an apparatus 40B for obtaining a transmission spectrum of the granular or fluid material 41 may include the spectrometer 12, a relay lightpipe 44, and the container 42 for holding the granular material. The vibration transducer 45 may be operably coupled to the container 42 for vibrating the container 42, or alternatively the vibration transducer 43 may vibrate the granular or fluid material directly. The additional light source 46 may illuminate the granular or fluid material 41 with illuminating light 47 through the window 45 while the vibration transducer 45 vibrates the container 42, thereby causing moving and mixing of the granular or fluid material 41.

The relay lightpipe 44 may include a slab of homogeneous transparent material extending between proximal 44A and distal 44B ends and configured for collecting signal light 48 emanating from the mixing and moving granular or fluid material 41 illuminated with the illuminating light 47, and conducting the signal light 48 from the distal end 44B to the proximal end 44A, for delivery to the spectral engine 6 of the spectrometer 12. The relay lightpipe 44 enables the spectrometer 12 to obtain the transmission spectrum of the granular material 41 at a distance D from the granular or fluid material 41, e.g. 10 cm or more.

The vibration transducer 43 of the apparatuses 40A and 40B of FIGS. 4A and 4B may vibrate the container 42 along a vertical axis 49, that is, along the length dimension of the relay lightpipe 14, or it may vibrate the container along a horizontal axis 48, that is, perpendicular to the relay lightpipe 14. The vibration transducer 43 may include a piezo transducer, an electromagnetic transducer, a rotating eccentric weight, or another suitable vibrating mechanism.

Figure 5B:
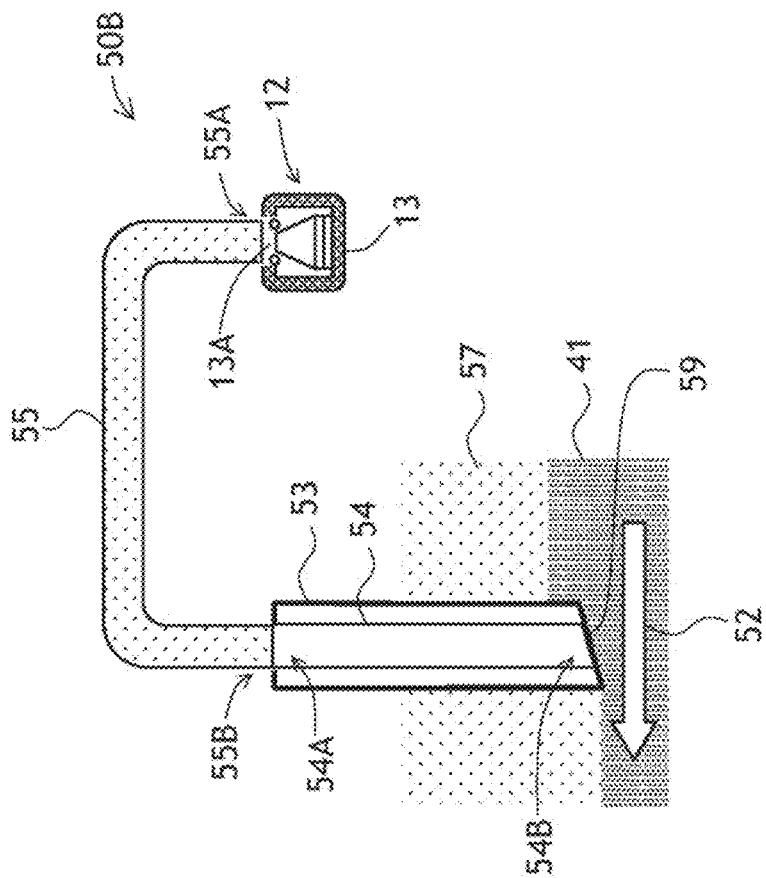
FIG. 5B illustrates a schematic side cross-sectional view of a variant of the apparatus of FIG. 5A including an optical fiber bundle.
Figure 5A:
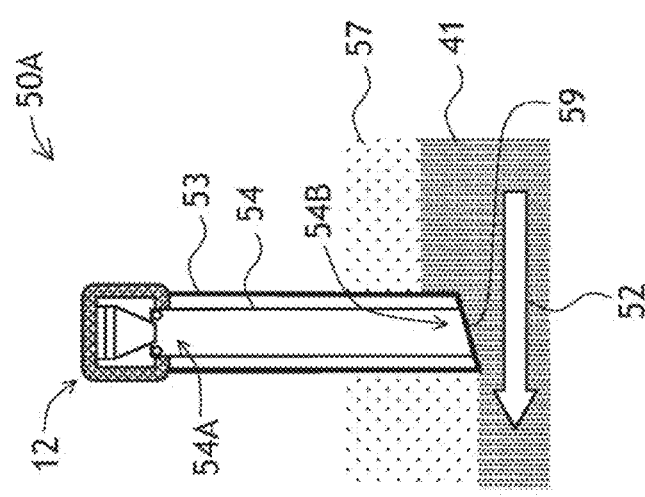
FIG. 5A illustrates a schematic side cross-sectional view of an apparatus for performing a spectral measurement of a flowing material.

Turning to FIG. 5A with further reference to FIG. 1A, an apparatus 50A for obtaining an optical spectrum of the flowing granular or fluid material 41 is shown. The granular or fluid material 41 may flow in a direction indicated by an arrow 52. The apparatus 50a is similar to the apparatus 10 of FIG. 1A, and a relay lightpipe 54 is analogous to the relay lightpipe 14 of FIG. 1A. A distal end 54B of the relay lightpipe 54 may be slanted, so that the flow of the granular or fluid material 41 impinges onto the slanted distal end 14B at an acute angle. Due to its geometry, the slanted distal end 54B exerts a pressure on the granular or fluid material 41 as the granular or fluid material 41 flows in the direction indicated by the arrow 52, which may facilitate illumination of the granular or fluid material 41 and/or the spectral data collection. An optional cover 53 having a window 59 may be provided for the relay lightpipe 54. For instance, where an aggressive medium 57 is present on top of the granular or fluid material 41, the cover 53 may protect the relay lightpipe 54 from corrosion by the aggressive medium 57.

Referring to FIG. 5B with further reference to FIG. 5A, an apparatus 50B for obtaining an optical spectrum of the flowing granular or fluid material 41 is similar to the apparatus 50A of FIG. 5A. The apparatus 50B may further include an optical fiber bundle 55 extending between its first 55A and second ends 55B. The first end 55A may be optically and mechanically coupled to the opening 15A (or transparent window) in the outer surface 13A of the housing 13, and the second end 55B may be optically and mechanically coupled to the proximal end 54A of the relay lightpipe 54. The optical fiber bundle 55 may be used with some other types of relay lightpipes, for example the optical fiber bundle 55 may be used in the apparatus 10 of FIG. 1A between the opening 15A and the proximal end 14A of the relay lightpipe 14. A bifurcated fiber bundle, not shown, may be used with the sectioned relay lightpipe 30 of FIGS. 3A, 3B.

Figure 6A:
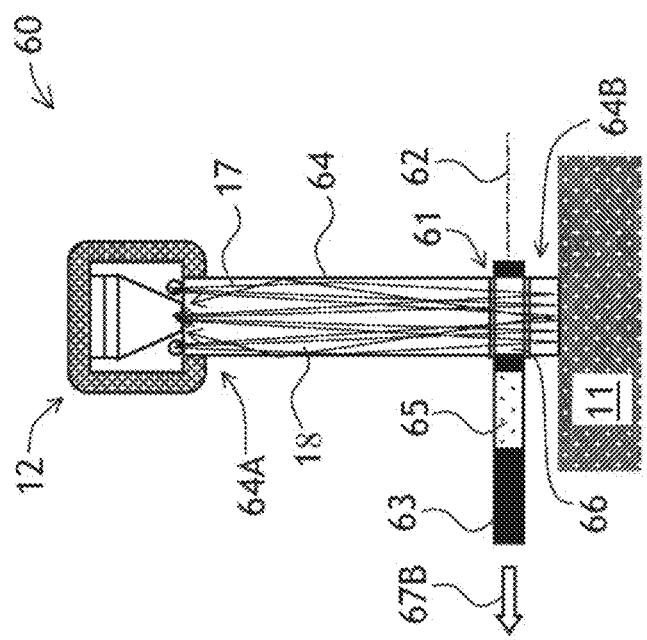
FIGS. 6A and 6B illustrate a self-calibrating variant of the apparatus of FIG. 1A.
Figure 6B:
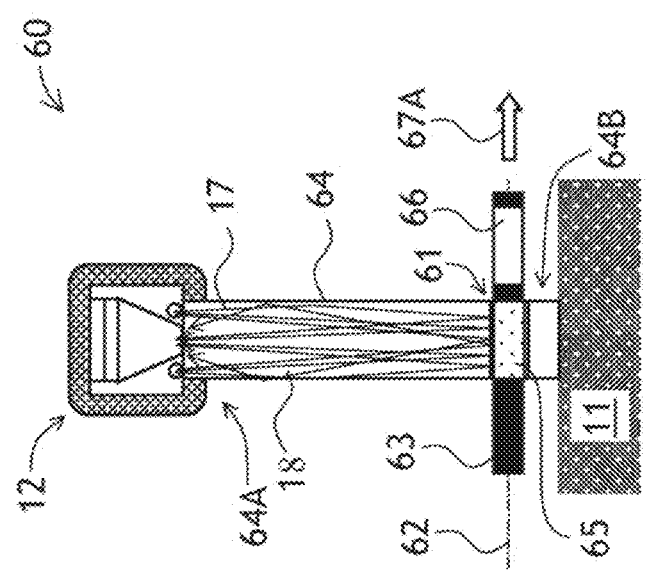

Referencing to FIGS. 6A and 6B with further reference to FIG. 1A, a self-calibrating apparatus 60 for obtaining a spectrum of the sample 11 is similar to the apparatus 10 of FIG. 1A. A relay lightpipe 64 of the apparatus 60 extends between its proximal 64A and distal 64B ends. The relay lightpipe 64 is generally similar to the relay lightpipe 14 of the apparatus 10 of FIG. 1A, one difference being that the relay lightpipe 64 may include a first opening 61. The first opening 61 runs through the relay lightpipe 64 in a direction 62 transversal to the illuminating light 17. The apparatus 60 may further include a calibration element 63 insertable into the first opening 61. The calibration element 63 may include a reflectance reference section 65.

In FIGS. 6A and 6B, the calibration element 63 is shown inserted into the first opening 61. In FIG. 6A, the reference section 64 is aligned, or registered, with the first opening 61, so as to reflect the illuminating light 17 back to the proximal end 64a of the relay lightpipe 64 for detection by the spectrometer 12. The purpose of the reflectance reference section is to enable the spectrometer 12 to obtain a spectrum, preferably a reflection spectrum, of a known sample. In one embodiment, the reflectance reference section 64 may include a white diffuse reflector, for example a Lambertian reflector. More than one reflectance reference section 65 may be provided in the calibration element 63.

The calibration element 63 may further include a through section 66, which may be aligned, or registered, with the first opening 61 when the calibration element 63 is inserted into the first opening. When the through section is registered with the first opening 61, the illuminating light 17 may propagate via the through section 66, so as to impinge onto the sample 11. The signal light 18 propagates from the distal end 64B, back via the through section 66, and is directed by the lightpipe 64 towards the spectrometer 12. In one embodiment, the through section 66 includes a transparent solid material, through which the illuminating light 17 and the signal light 18 may propagate.

In FIGS. 6A and 6B, the through section 66 and the reflectance reference, section 65 of the calibration element 63 are shown disposed proximate each other along the calibration element 63, that is, along the transversal direction 62. When a calibration is required, the calibration element is shifted in the transversal direction 62 as illustrated by an arrow 67A in FIG. 6A. To take a measurement, the calibration element 63 is shifted in the transversal direction 62 as illustrated by an arrow 67B in FIG. 6B. Other configurations are possible, for example the calibration element 63 may generally have a circular cross-section for inserting into the matching opening 61, which may have a matching diameter. The calibration element 63 may base a portion with a square cross-section, not shown, with the reflectance reference section 65 being on one of the sides of the square portion, or on opposite sides of the square portion.

Figure 7:
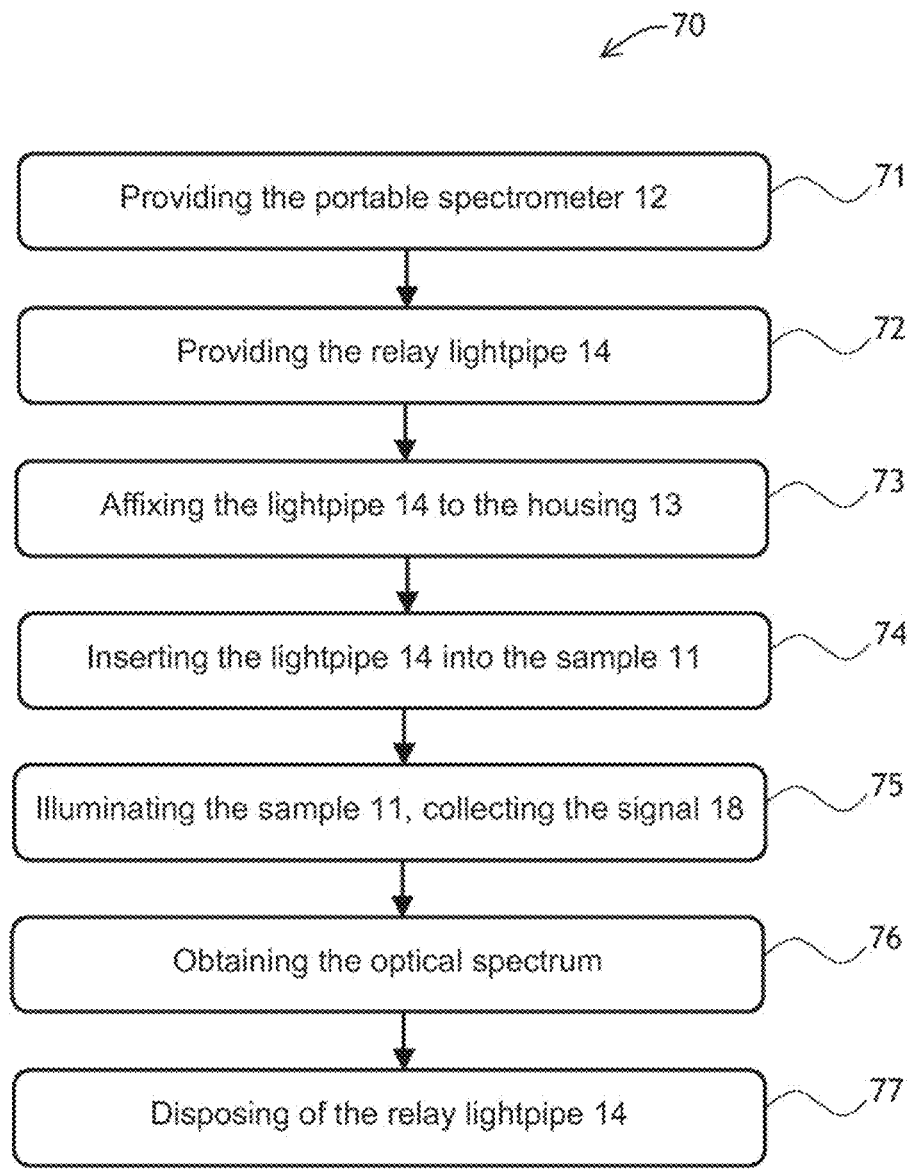
FIG. 7 illustrates a method of the present disclosure for obtaining an optical spectrum of a sample.

Referring now to FIG. 7, a method 70 for obtaining an optical spectrum of the sample 11, e.g. the granular material 41 or another material e.g. a solid or liquid material, may include a step 71 of providing the spectrometer 12 described above with reference to FIGS. 1A-1C, 2, and 3A-3B. In a next step 72, the relay lightpipe 14 may be provided. The relay lightpipe 14 may be configured for unconstrained propagation of light in bulk of the relay lightpipe 14 between the proximal 14A and distal 14B ends, as explained above. Alternatively the sectioned relay lightpipe 34 of FIGS. 3A and 3B may be provided.

In a next step 73, the relay lightpipe 14 is affixed to the housing 13 so that the proximal end 14A is disposed adjacent the opening 15A or transparent window, thereby optically coupling the relay lightpipe 14 to the light source 16 and the spectral engine 6 of the spectrometer 12. In a following step 74, the distal end 14B of the relay lightpipe 14 is brought near, into a contact, or inserted into the sample 11. In a next, signal collection step 75, the illuminating light 17 is conducted within the relay lightpipe 14 from the proximal end 14A to the distal end 14B for illuminating the sample 11, and the signal light 18 emanating from the sample 11 illuminated with the illuminating light 17 is collected. The signal light 18 may include e.g. a portion of the illuminating light 17 reflected by the sample 11, a fluorescence light, a phosphorescence light, etc. The signal light 18 is conducted by the relay lightpipe 14 back from the distal end 14B to the proximal end 14A and further to the spectral engine 6. In a next step 76, the optical spectrum of the sample 11 is obtained by the spectrometer 12. The relay lightpipe 14 enables the optical spectrum to be collected at a distance from the sample 11. A calibration may be performed before bringing the relay lightpipe 14 to the sample 11 in the step 74, e.g. by using the self-calibrating apparatus 60 of FIGS. 6A and 6B.

When the sample 11 includes the granular material 41, the granular material 41 may be vibrated in the container 42 (FIG. 4A) in the signal collection step 75. When the sample 11 includes a hazardous material, e.g. a chemically aggressive substance, and the measurement involved a physical contact between the relay lightpipe 14 and the sample 11, the relay lightpipe 14 may be disposed of in an optional step 77.

The present disclosure is not to be limited in scope by the specific embodiments described herein. Indeed, other various embodiments and modifications, in addition to those described herein, will be apparent to those of ordinary skill in the art from the foregoing description and accompanying drawings. Thus, such other embodiments and modifications are intended to fall within the scope of the present disclosure. Further, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. An apparatus comprising:
   a container for holding a sample,
   the container including a window that is positioned at a bottom of the container;
   a vibration transducer, operably coupled to the bottom of the container, for vibrating the container,
   the vibration transducer being capable of vibrating both in a direction along a vertical axis relative to the bottom of the container and in a direction along a horizontal axis relative to the bottom of the container; and
   a light source optically coupled to the window,
   the light source illuminating the sample via the window while the vibration transducer vibrates the container.

2. The apparatus of claim 1, where the sample comprises a granular or fluid material.

3. The apparatus of claim 1, where the container further includes an opening to receive a relay lightpipe into the sample.

4. The apparatus of claim 1, further comprising:
   a relay lightpipe that obtains an optical spectrum of the sample while the vibration transducer vibrates the container.

5. The apparatus of claim 1, further comprising:
   a relay lightpipe that includes a slab of homogenous transparent material extending between a proximal end of the relay lightpipe and a distal end of the relay lightpipe.

6. The apparatus of claim 5, where the slab of homogenous transparent material includes a lens element optically coupled to the distal end of the relay lightpipe.

7. The apparatus of claim 1, further comprising:
   a relay lightpipe to:
   collect signal light emanating from mixing and moving of the sample that is caused by vibrating the sample.

8. The apparatus of claim 7, where the relay lightpipe is further to:
   conduct the signal light from a distal end of the relay lightpipe to a proximal end of the relay lightpipe.

9. The apparatus of claim 8, where the distal end of the relay lightpipe is chiseled.

10. The apparatus of claim 1, where the vibration transducer vibrates the container along the vertical axis that is along a length dimension of a relay lightpipe.

11. The apparatus of claim 1, where the vibration transducer vibrates the container along the horizontal axis that is perpendicular to a relay lightpipe.

12. The apparatus of claim 1, where the vibration transducer comprises one of:
    a piezo transducer,
    an electromagnetic transducer, or
    a rotating eccentric weight.

13. A method comprising:
    vibrating, using a vibration transducer, a container that includes a window that is positioned at a bottom of the container,
    the vibration transducer being operably coupled to the bottom of the container,
    the vibration transducer being capable of vibrating both in direction along a vertical axis relative to the bottom of the container and in a direction along a horizontal axis relative to the bottom of the container, and
    the container holding a sample; and
    illuminating, using a light source optically coupled to the window, the sample via the window while the container is vibrating.

14. The method of claim 13, where the sample comprises a granular or fluid material.

15. The method of claim 13, further comprising:
    obtaining, using a relay lightpipe, an optical spectrum of the sample while the container is vibrating.

16. The method of claim 13, further comprising:
    collecting, using a relay lightpipe, signal light emanating from mixing and moving of the sample that is caused by vibrating of the container.

17. The method of claim 16, further comprising:
    collecting, using a slab of homogenous transparent material extending between a proximal end of the relay lightpipe and a distal end of the relay lightpipe, the signal light from the distal end of the relay lightpipe to the proximal end of the relay lightpipe.

18. The method of claim 17, where the distal end of the relay lightpipe is lensed.

19. The method of claim 17, where the slab of homogenous transparent material includes a lens element optically coupled to the distal end of the relay lightpipe.

20. The method of claim 13, where vibrating the container comprises:

vibrating the container along the vertical axis that is along a length dimension of a relay lightpipe.

* * * * *